(12) United States Patent
Lamego

(10) Patent No.: US 10,219,754 B1
(45) Date of Patent: Mar. 5, 2019

(54) MODULATION AND DEMODULATION TECHNIQUES FOR A HEALTH MONITORING SYSTEM

(71) Applicant: Apple Inc., Cupertino, CA (US)

(72) Inventor: Marcelo M. Lamego, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/621,268

(22) Filed: Feb. 12, 2015

Related U.S. Application Data

(60) Provisional application No. 62/047,818, filed on Sep. 9, 2014.

(51) Int. Cl.
*A61B 5/00* (2006.01)

(52) U.S. Cl.
CPC .......... *A61B 5/7228* (2013.01); *A61B 5/0059* (2013.01); *A61B 5/681* (2013.01); *A61B 5/7203* (2013.01); *A61B 5/725* (2013.01); *A61B 5/7225* (2013.01); *A61B 5/7278* (2013.01)

(58) Field of Classification Search
CPC ............................ A61B 5/0059; A61B 5/0084
See application file for complete search history.

(56) References Cited

U.S. PATENT DOCUMENTS

| | | | | |
|---|---|---|---|---|
| 5,349,952 A | * | 9/1994 | McCarthy | A61B 5/0059 356/41 |
| 2012/0253155 A1 | * | 10/2012 | Diab | A61B 5/14551 600/324 |

* cited by examiner

*Primary Examiner* — Hien Nguyen
(74) *Attorney, Agent, or Firm* — Brownstein Hyatt Farber Schreck, LLP

(57) ABSTRACT

An electronic device includes one or more light sources for emitting light toward a body part of a user and one or more optical sensors for capturing light samples while each light source is turned on and for capturing dark samples while the light source(s) are turned off. A signal produced by the one or more optical sensors is demodulated produce multiple demodulated signals. Each demodulated signal is received by one or more decimation stages to produce a signal associated with each light source. Each signal associated with the light source(s) is analyzed to estimate or determine a physiological parameter of the user.

6 Claims, 9 Drawing Sheets

MODULATION AND DEMODULATION TECHNIQUES FOR A HEALTH MONITORING SYSTEM

CROSS-REFERENCE TO RELATED APPLICATION

This application claims the benefit under 35 U.S.C. § 119(e) of U.S. Provisional Patent Application No. 62/047,818, filed Sep. 9, 2014, entitled "Modulation and Demodulation Techniques for a Health Monitoring System," the entirety of which is incorporated herein by reference.

TECHNICAL FIELD

The present invention relates generally to health monitoring systems, and more particularly to modulation and demodulation techniques for a health monitoring system that includes one or more optical sensors.

BACKGROUND

Health monitoring devices, such as fitness and wellness devices, are capable of measuring a variety of physiological parameters and waveforms non-invasively via optical sensing. Light is applied to a measurement site, such as a user's wrist, finger, and ear, and the light is absorbed and scattered throughout the skin. An optical sensor in the health monitoring device captures the light that is reflected from or transmitted through the skin. The optical sensor, however, is subject to interferences caused by fluorescent bulbs, sun light, the electricity grid or network, and motion artifacts that are caused by the relative motion between the optical sensor and the user's measurement site. Thus, the light collected by the light sensor contains a component from the measurement site and component from one or more interferences. To estimate the physiological parameter and waveform, the optical sensor coverts the collected light into electrical signals, and the signal that represents the interference component is typically subtracted from the signal representing the measurement site component. After subtraction, only the component from the measurement site should remain, which is the component that is used to estimate the physiological parameter. However, subtraction cannot be performed instantaneously. A time delay exists between sampling the light and subtracting the interference component. The time delay can result in the creation of aliases in the signal, and the aliases produce errors in the estimation of the physiological parameter.

SUMMARY

In one aspect, an electronic device includes one or more light sources for emitting light toward a body part of a user and one or more optical sensors for capturing light samples while each light source is turned on and for capturing dark samples while the light source(s) are turned off. A signal produced by the one or more optical sensors is demodulated produce multiple demodulated signals. Each demodulated signal is received by one or more decimation stages to produce a signal associated with each light source. A demultiplexer and multiplier circuit operably can be connected to an output of the decimation stage. The demultiplexer separates the signals by each associated light source and the multiplier multiplies each signal by one or more respective weights. The weights adjust the signals for variations in temperature and operating parameters of various components in the electronic device. Each signal associated with the light source(s) is analyzed to estimate or determine a physiological parameter of the user.

In another aspect, a method for processing the signal received from the light sensor can include capturing multiple light samples while each light source emits light toward the body part of the user and converting the multiple light samples into the signal. The light sources can be modulated (e.g., turned on and off) according to a particular modulation pattern. The signal produced by the optical sensor is then demodulated to produce multiple demodulated signals. Each demodulated signal is associated with a particular light source. Each demodulated signal is then be processed by at least one decimation stage. In one embodiment, each decimation stage includes a low pass filter that receives a demodulated signal and a decimation circuit operably connected to an output of the low pass filter. A demultiplexer and multiplier circuit may then process the signals. Each signal associated with the light source(s) is analyzed to estimate or determine a physiological parameter of the user.

In yet another aspect, a method for operating an electronic device that includes multiple light sources, an optical sensor, and a processing device operably connected to the optical sensor can include turning on each light source one at a time and emitting light toward a body part of a user and capturing multiple light samples while each light source emits light toward the body part of the user and converting the multiple light samples into a signal. The signal is converted into a digital signal, and the digital signal is demodulated to produce multiple demodulated signals. Each demodulated signal is then processed by at least one decimation stage. In one embodiment, each decimation stage includes a low pass filter that receives a demodulated signal and a decimation circuit operably connected to an output of the low pass filter. Each signal associated with the light source(s) is analyzed to estimate or determine a physiological parameter of the user.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures.

DETAILED DESCRIPTION

Figure 1:
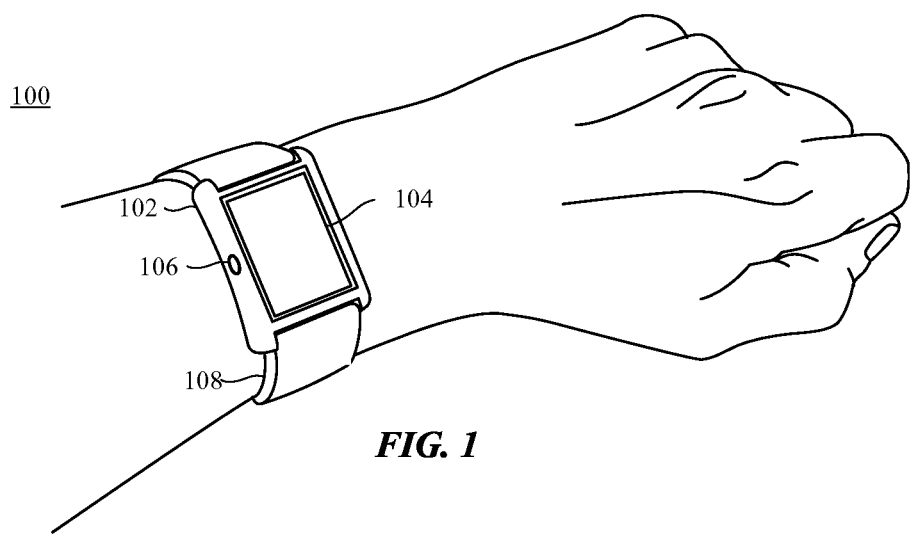
FIG. 1 a perspective front view of one example of an electronic device that provides health-related information.

Embodiments described herein provide modulation and demodulation techniques that reduce or eliminate undesired interferences and produce demodulated signals that can be analyzed to estimate a physiological parameter of a user. A time multiplexed modulation pattern is used to turn the light sources on and off and to cause the optical sensor to capture multiple light and dark samples. Demodulation operations are applied to the signal produced by the optical sensor to produce a signal associated with each light source. In general, the demodulation operation can be $$\sin 2\pi \frac{kt}{N} \text{ or } \cos 2\pi \frac{kt}{N}.$$

The demodulated signals may then be processed by one or more decimation stages. Each decimation stage can include a low pass filter and a decimation circuit.

Any suitable type of electronic device can include a health monitoring system. Example electronic devices include, but are not limited to, a smart telephone, a headset, a pulse oximeter, a digital media player, a tablet computing device, and a wearable electronic device. A wearable electronic device can include any type of electronic device that can be worn on a limb of a user. The wearable electronic device can be affixed to a limb or body part of a user, such as a wrist, an arm, a finger, a leg, an ear, or a chest. In some embodiments, the wearable electronic device is worn on a limb of a user with a band that attaches to the body and includes a holder or case to detachably or removably hold the electronic device, such as an armband, an ankle bracelet, a leg band, and/or a wristband. In other embodiments, the wearable electronic device is permanently affixed or attached to a band, and the band attaches to the body of the user.

As one example, a wearable electronic device can be implemented as a wearable health assistant that provides health-related information (whether real-time or not) to the user, authorized third parties, and/or an associated monitoring device. The wearable health assistant may be configured to provide health-related information or data such as, but not limited to, heart rate data, blood pressure data, temperature data, blood oxygen saturation level data, diet/nutrition information, medical reminders, health-related tips or information, or other health-related data. The associated monitoring device may be, for example, a tablet computing device, phone, personal digital assistant, computer, and so on.

As another example, the electronic device can be configured in the form of a wearable communications device. The wearable communications device may include a processor coupled with or in communication with a memory, one or more sensors, one or more communication interfaces, output devices such as displays and speakers, one or more input devices, and a health monitoring system. The communication interface(s) can provide electronic communications between the communications device and any external communication network, device or platform, such as but not limited to wireless interfaces, Bluetooth interfaces, USB interfaces, Wi-Fi interfaces, TCP/IP interfaces, network communications interfaces, or any conventional communication interfaces. The wearable communications device may provide information regarding time, health, statuses or externally connected or communicating devices and/or software executing on such devices, messages, video, operating commands, and so forth (and may receive any of the foregoing from an external device), in addition to communications.

Referring now to FIG. 1, there is shown a perspective view of one example of an electronic device that provides health-related information. In the illustrated embodiment, the electronic device 100 is implemented as a wearable communication device. Other embodiments can implement the electronic device differently. As described earlier, the electronic device can be a smart telephone, a gaming device, a digital music player, a device that provides time, a health assistant, and other types of electronic devices that provide health-related information.

The electronic device 100 includes an enclosure 102 at least partially surrounding a display 104 and one or more buttons 106 or input devices. The enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. A button 106 can take the form of a home button, which may be a mechanical button, a soft button (e.g., a button that does not physically move but still accepts inputs), an icon or image on a display or on an input region, and so on. Other buttons or mechanisms can be used as input/output devices, such as a speaker, a microphone, an on/off button, a mute button, or a sleep button. In some embodiments, the button or buttons 106 can be integrated as part of a cover glass of the electronic device.

The electronic device 100 can be permanently or removably attached to a band 108. The band 108 can be made of any suitable material, including, but not limited to, leather, metal, rubber or silicon, fabric, and ceramic. In the illustrated embodiment, the band is a wristband that wraps around the user's wrist. The wristband can include an attachment mechanism (not shown), such as a bracelet clasp, Velcro, and magnetic connectors. In other embodiments, the band can be elastic or stretchy such that it fits over the hand of the user and does not include an attachment mechanism.

Figure 2:
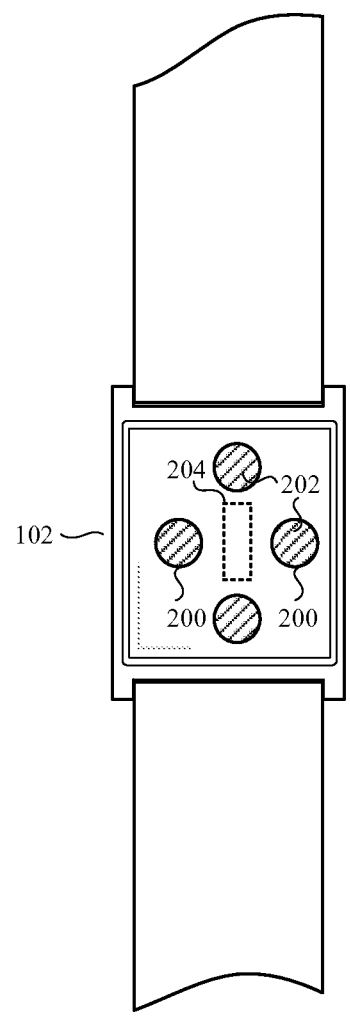
FIG. 2 depicts a back view of the electronic device 100 shown in FIG. 1.

FIG. 2 depicts a back view of the electronic device 100 shown in FIG. 1. As described earlier, the electronic device can include one or more sensors, and at least one of these sensors may provide health-related information. As one example, the wearable communication device can include an optical sensor, such as a photoplethysmography (PPG) sensor. A PPG sensor uses light to measure changes in the volume of a part of a user's body. As the light passes through the user's skin and into the underlying tissue, some light is reflected, some is scattered, and some light is absorbed, depending on what the light encounters. Blood can absorb light more than surrounding tissue, so less reflected light will be sensed by the PPG sensor when more blood is present. The user's blood volume increases and decreases with each heartbeat. A PPG sensor detects changes in blood volume based on the reflected light, and one or more physiological parameters of the user can be determined by analyzing the reflected light. Example physiological parameters include, but are not limited to, heart rate and respiration.

The electronic device 100 includes one or more apertures 200 in the enclosure 102. Each aperture is associated with a light source 202. In one embodiment, each light source is implemented as a light-emitting diode (LED). Four apertures 200 and four light sources 202 are used in the illustrated embodiment. Other embodiments can include any number of light sources 200. For example, two light sources can be used in some embodiments.

The light sources 202 can operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user will be determined, the light sources emit light toward the user's skin and the optical sensor 204 senses an amount of reflected light. The optical sensor 204 may sense the reflected light through an aperture (not shown) that is formed in the electronic device. As will be described in more detail later, a modulation pattern can be used to turn the light sources on and off and sample or sense the reflected light.

Figure 3:
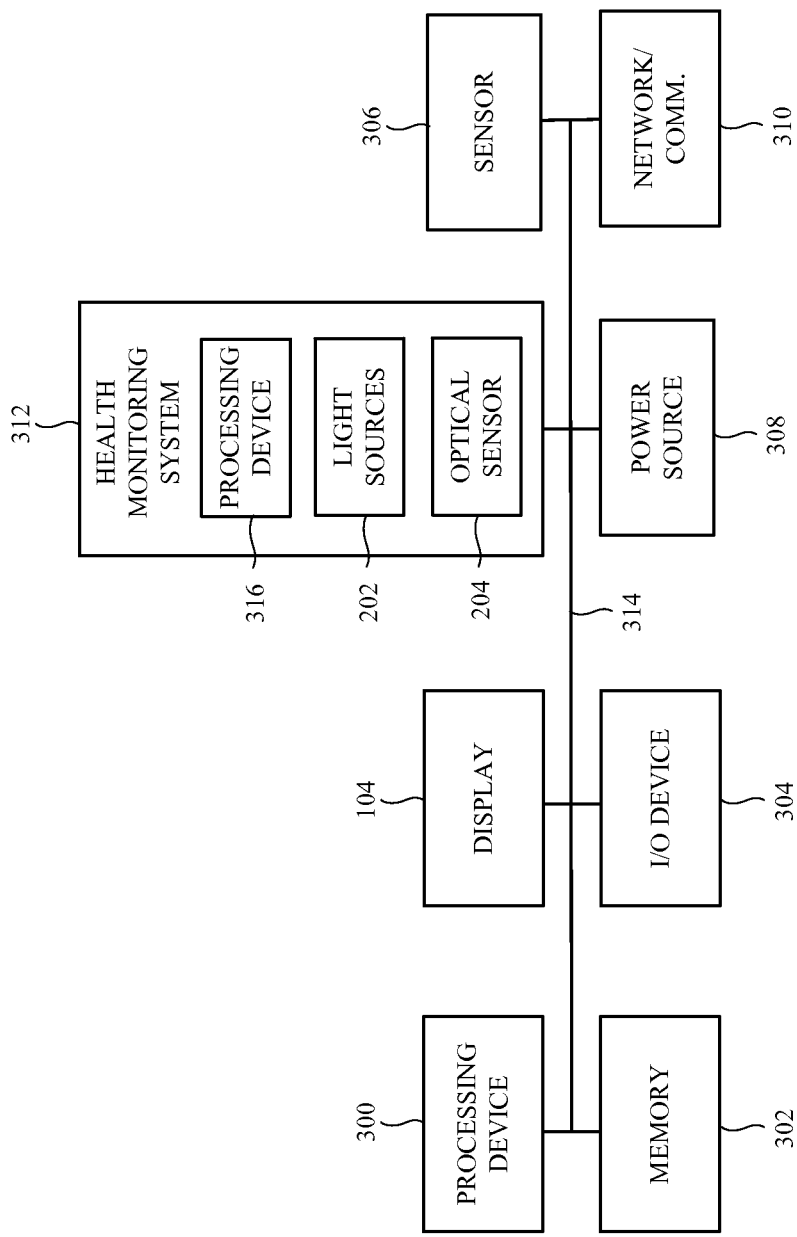
FIG. 3 is an illustrative block diagram of the electronic device 100 shown in FIGS. 1 and 2.

FIG. 3 is an illustrative block diagram of the electronic device 100 shown in FIG. 1. The electronic device 100 can include the display 104, one or more processing devices 300, memory 302, one or more input/output (I/O) devices 304, one or more sensors 306, a power source 308, a network communications interface 310, and a health monitoring system 312. The display 104 may provide an image or video output for the electronic device 100. The display may also provide an input surface for one or more input devices, such as, for example, a touch sensing device and/or a fingerprint sensor. The display 104 may be substantially any size and may be positioned substantially anywhere on the electronic device 100.

The processing device 300 can control some or all of the operations of the electronic device 100. The processing device 300 can communicate, either directly or indirectly with substantially all of the components of the electronic device 100. For example, a system bus or signal line 314 or other communication mechanisms can provide communication between the processing device(s) 300, the memory 302, the I/O device(s) 304, the sensor(s) 306, the power source 308, the network communications interface 310, and/or the health monitoring system 312. The one or more processing devices 300 can be implemented as any electronic device capable of processing, receiving, or transmitting data or instructions. For example, the processing device(s) 200 can each be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitably configured computing element or elements.

The memory 302 can store electronic data that can be used by the electronic device 100. For example, a memory can store electrical data or content such as, for example, audio and video files, documents and applications, device settings and user preferences, timing and control signals or data for the health monitoring system 312, data structures or databases, and so on. The memory 302 can be configured as any type of memory. By way of example only, the memory can be implemented as random access memory, read-only memory, Flash memory, removable memory, or other types of storage elements, or combinations of such devices.

The one or more I/O devices 304 can transmit and/or receive data to and from a user or another electronic device. One example of an I/O device is button 106 in FIG. 1. The I/O device(s) 304 can include a display, a touch sensing input surface such as a track pad, one or more buttons, one or more microphones or speakers, one or more ports such as a microphone port, and/or a keyboard.

The electronic device 100 may also include one or more sensors 306 positioned substantially anywhere on the electronic device 100. The sensor or sensors 306 may be configured to sense substantially any type of characteristic, such as but not limited to, images, pressure, light, touch, heat, position, motion, and so on. For example, the sensor(s) 308 may be an image sensor, a heat sensor, a light or optical sensor, a pressure transducer, a magnet, a gyroscope, an accelerometer, and so on.

The power source 308 can be implemented with any device capable of providing energy to the electronic device 100. For example, the power source 308 can be one or more batteries or rechargeable batteries, or a connection cable that connects the remote control device to another power source such as a wall outlet.

The network communication interface 310 can facilitate transmission of data to or from other electronic devices. For example, a network communication interface can transmit electronic signals via a wireless and/or wired network connection. Examples of wireless and wired network connections include, but are not limited to, cellular, Wi-Fi, Bluetooth, IR, and Ethernet.

The health monitoring system 312 can include the light sources 202, one or more optical sensors 204, and a processing device 316. The processing device 316 may be any suitable type of processing device. In one embodiment, the processing device 316 is a digital signal processor. The processing device 316 may receive signals from the optical sensor(s) 204 and processes the signals to correlate the signal values with a physiological parameter of the user. As one example, the processing device can apply one or more demodulation operations to the signals received from the optical sensor. Additionally, the processing device may control the modulation (e.g., turning on and off) of the light sources 202 according to a given modulation pattern. In one embodiment, one or more modulation patterns may be stored in memory 302 and accessed by the processing device 316 to modulate the light sources 202.

As discussed earlier, the light sources can emit light in the visible and/or infrared wavelength ranges. The optical sensor or sensors 204 is implemented as a photodetector that senses light and converts the light into an electrical signal that represents the amount of light sensed by the photodetector. In one embodiment, the photodetector can be a photodiode. Other embodiments can use a different type of photodetector, such as a phototube or photoresistor.

In another embodiment, the processing device 316 is not included in the health monitoring system 312 and the processing device 300 receives signals from the optical sensor(s) 204 and processes the signals to correlate the signal values with a physiological parameter of the user. Additionally or alternatively, the processing device 300 can control the operations of the light sources (e.g., turn on and off). One or more modulation patterns may be stored in memory 302 and accessed by the processing device 300 to modulate the light sources 202.

It should be noted that FIGS. 1-3 are illustrative only. In other examples, an electronic device may include fewer or more components than those shown in FIG. 3. Additionally or alternatively, the electronic device can be included in a system and one or more components shown in FIG. 3 are separate from the electronic device but in communication with the electronic device. For example, an electronic device may be operatively connected to, or in communication with a separate display. As another example, one or more applications or data can be stored in a memory separate from the electronic device. As another example, a processing device in communication with the electronic device can control various functions in the electronic device and/or process data received from the electronic device. In some embodiments, the separate memory and/or processing device can be in a cloud-based system or in an associated monitoring device.

Figure 4:
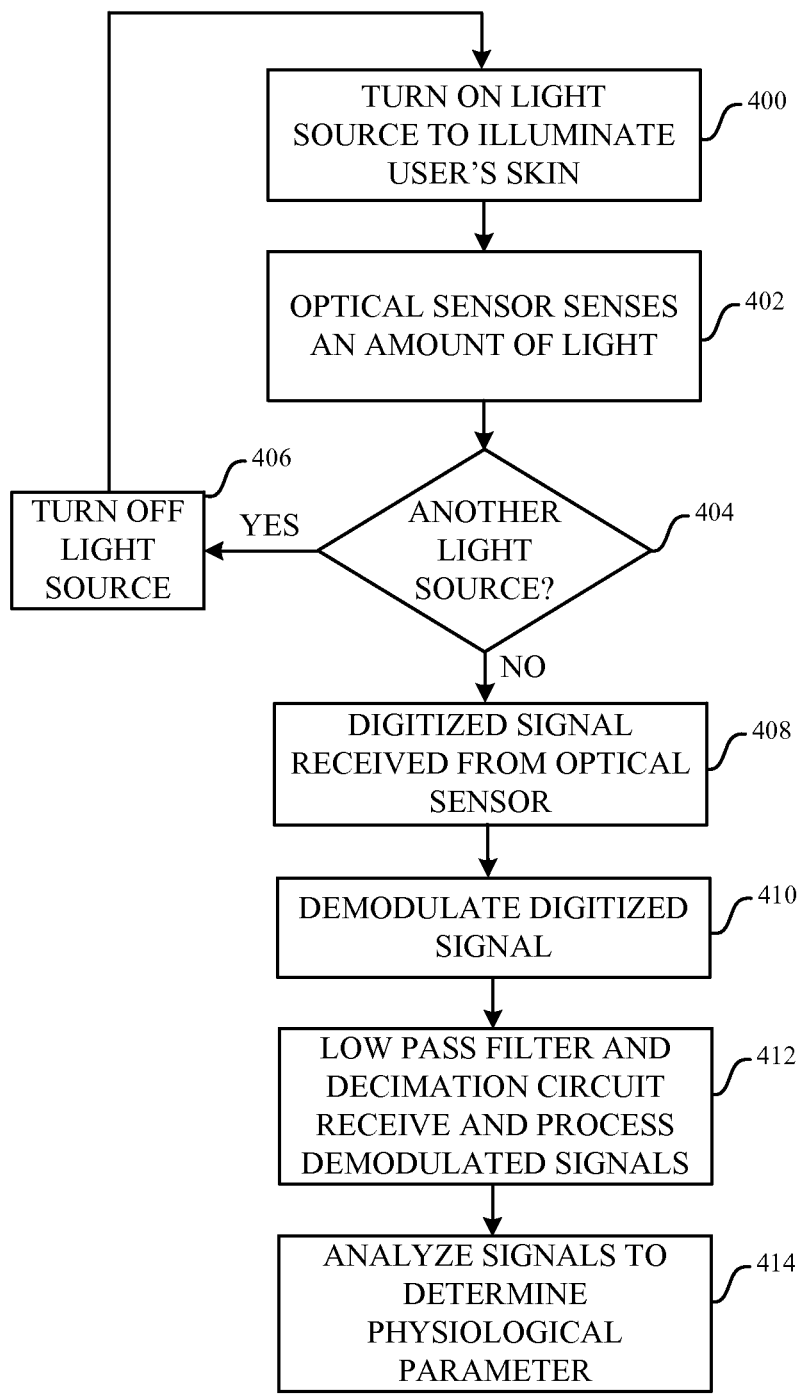
FIG. 4 is a flowchart of one example method of operating the health monitoring system 312 in FIG. 3.

Referring now to FIG. 4, there is shown a flowchart of one example method of operating the health monitoring system 312 in FIG. 3. Initially, a light source is turned on to illuminate the user's skin and the optical sensor senses an amount of reflected or transmitted light (blocks 400, 402). A determination can then be made at block 404 as to whether or not another light source is to be turned on. For example, in one embodiment, the light sources are turned on sequentially and the optical sensor senses the light multiple times while each light source is turned on.

If another light source is to be turned on, the process passes to block 406 where the light source that is currently turned on is turned off. The method then returns to block 400 and repeats until all of the light sources have been turned on and the optical sensor has obtained light samples.

When a determination is made at block 404 that all of the light sources have been turned on, the process continues at block 408 where the signal received from the optical sensor is digitized by inputting the signal into an analog-to-digital converter. The digitized signal is then demodulated at block 410. Demodulating the signal produces multiple demodulated signals, with a demodulated signal associated with each light source. Each demodulated signal is then received and processed by a low pass filter and a decimation circuit (block 412).

The signals may then be analyzed at block 414 to determine or estimate a physiological parameter of the user. As described earlier, in one embodiment the signals can be analyzed to determine a heart rate of the user. As one example, the processing device 316 can analyze the signals to estimate a physiological parameter of the user. In another example, the processing device 300 can analyze the signals to determine a physiological parameter of the user. And in yet another example, both processing devices 300, 316 can perform various steps in the analysis to estimate a physiological parameter of the user.

In other embodiments, the light source need not be turned off or on entirely. Instead, certain embodiments may modulate the brightness of the light source in place of or in addition to the turning of lights on and off. In some embodiments, certain light sources may be turned on and off while other light sources are alternately dimmed and brightened.

Figure 5:
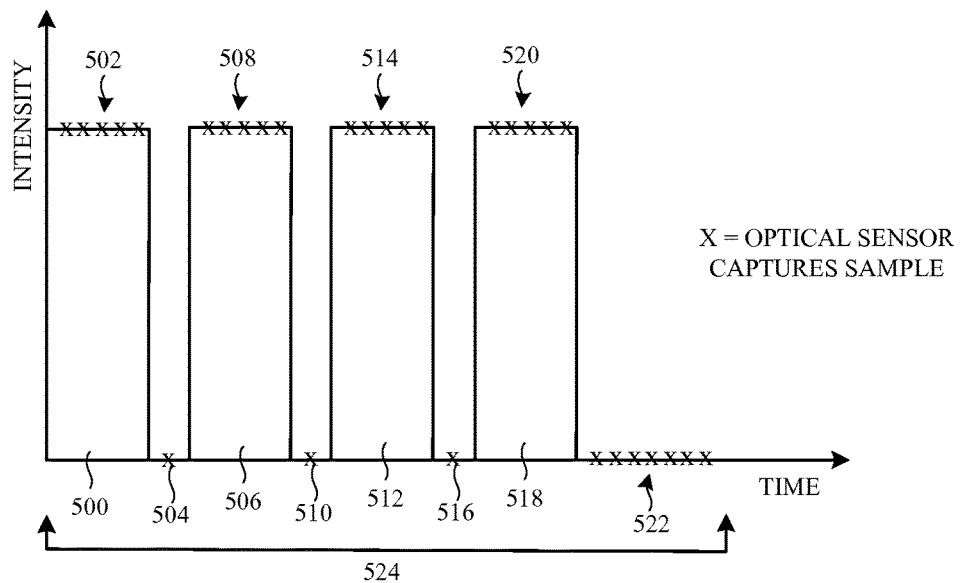
FIGS. 5-6 depict example modulation patterns suitable for use in blocks 400 and 402 in FIG. 4.
Figure 6:
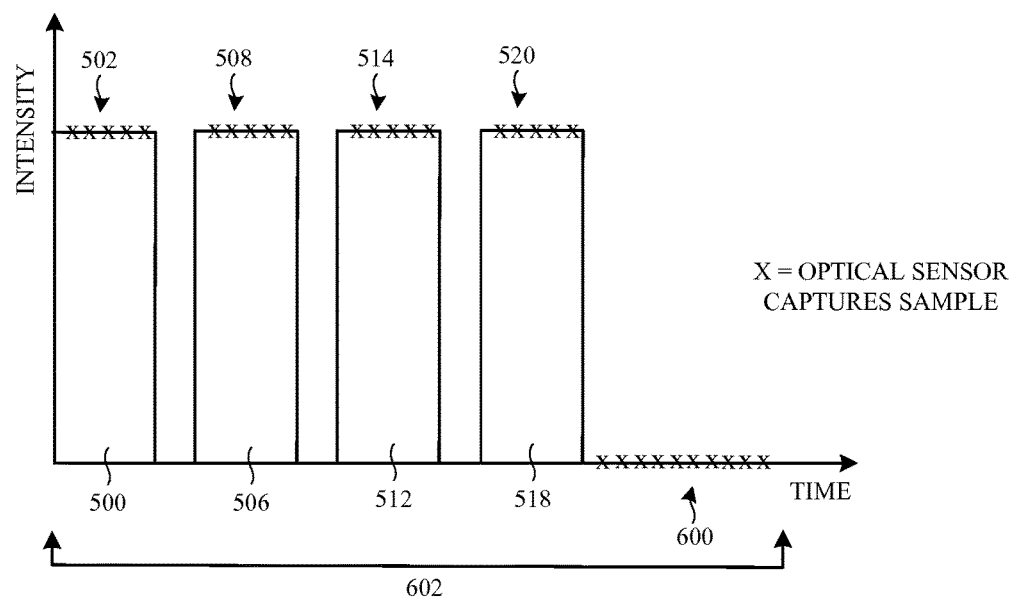

FIGS. 5-6 depict example modulation patterns suitable for use in blocks 400 and 402 in FIG. 4. FIGS. 5 and 6 are described with reference to a health monitoring system that includes four light sources. As described earlier, other embodiments can include fewer or more light sources. The embodiments described hereinafter are described with reference to a thirty sample modulation cycle operating at 4096 hertz. This is provided by way of example and is not required. Other modulation cycle frequencies and/or sampling frequencies may be selected. For example, the modulation cycle frequencies may range, as a non-limiting example, from one hundred hertz to several hundred kilohertz.

In many examples, the modulation cycle frequency and the sampling frequency may be interrelated. For example, certain embodiments may be limited by hardware or software to a particular maximum sampling frequency. In such an example, the modulation cycle frequency may be selected such that the transmitted signal can be adequately reconstructed. In some cases, the modulation cycle may be less than half the sampling rate. Stated another way, if a certain embodiment requires a particular bandwidth, the sampling frequency may be at least twice the selected maximum frequency of the selected bandwidth.

Other embodiments can obtain a different number of samples and/or operate at a different frequency. The frequency may be determined based on a number of factors, one of which is the harmonics of the electrical network or grid. For example, when an electrical network produces a signal at 60 Hz, the harmonics are multiples of 60 (e.g., 120 Hz, 180 Hz, 240 Hz, etc.). Also, some electrical networks produce a signal at 50 Hz, and the harmonics of multiples of 50 Hz (e.g., 100 Hz, 150 Hz, 200 Hz, etc.).

Additionally, some electrical networks can be less reliable at generating a signal with a specific frequency, and the frequency may vary by a certain amount or deviation (e.g., a frequency of 60 Hz may operate at 60+/−1% Hz). And the deviation increases with each harmonic. Thus, in one embodiment, the frequency of the modulation cycle is selected to be in a harmonic gap that exists between the various harmonics and harmonic deviations of at least one electrical network.

The illustrated modulation patterns are time-multiplexed modulation patterns that drive the light sources. The time periods when the light sources are turned on and off are multiplexed in time. In FIG. 5, the first light source is turned on for the time period 500. The other three light sources are turned off during the time period 500. An optical sensor captures a light sample multiple times 502 during the time period 500. In the illustrated embodiment, the optical sensor obtains five light samples 502. The first light source is then turned off and the optical sensor captures the light at time 504. A light sample obtained when all of the light sources are turned off is known as a dark sample.

The second light source is then turned on for the time period 506. Again, the other three light sources are turned off during the time period 506. The optical sensor captures multiple light samples 508 during the time period 506. In the illustrated embodiment, the optical sensor obtains five samples 508. The second light source is then turned off and the optical sensor captures a dark sample at time 510.

Similarly, only the third light source is turned on for the time period 512, and the optical sensor senses an amount of light multiple times 514 (e.g., five times) during the time period 512. The third light source is then turned off and the optical sensor captures a dark sample at time 516.

The fourth light source is then turned on for the time period 518, and the optical sensor obtains multiple light samples 520 (e.g., five times) during the time period 518. The fourth light source is then turned off and the optical sensor captures multiple dark samples 522. In the illustrated embodiment, the optical sensor obtains seven dark samples 522. Thus, the optical sensor captures thirty samples during one modulation cycle 524. The modulation cycles can repeat a given number of times when estimating a physiological parameter. As described earlier, the modulation cycle can have a frequency of 4096 Hz in one embodiment.

The modulation pattern in FIG. 6 is similar to the modulation pattern in FIG. 5 except that the optical sensor does not capture dark samples in between the time periods when a light source is turned on. In other words, the optical sensor does not sense dark samples at times 504, 510, and 516. The light sensor obtains multiple dark samples 600 after the time period 518 has ended (after the fourth light source is turned off). In the illustrated embodiment, the light sensor captures ten dark samples 600. Like the FIG. 5 embodiment, the optical sensor obtains thirty samples during one modulation cycle 602.

The analog signal produced by the optical sensor includes information associated with all four light sources. Thus, in one embodiment, the analog signal is demodulated by a single optical sensor to produce four signals. In some cases, each signal is associated with a specific light source. In other examples, two optical sensors may be used to generate eight signals associated with the four light sources. In some cases, the two optical sensors may be physically separated so as to measure light associated with the four light sources from different points along the user's skin. In other embodiments, more than two optical sensors may be used.

Figure 7:
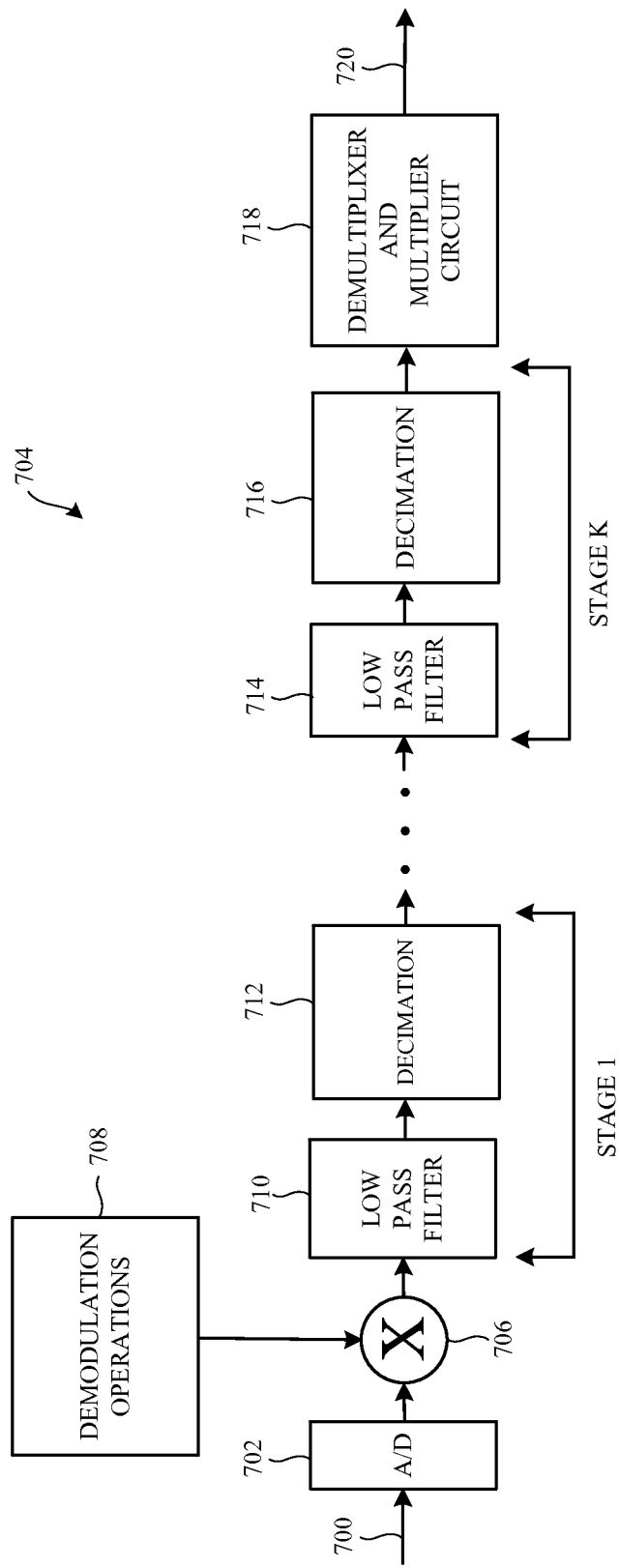
FIG. 7 is a data flow diagram of a processing channel that performs blocks 408, 410, and 412 in FIG. 4.

FIG. 7 is a data flow diagram of an illustrative processing channel that performs blocks 408, 410, and 412 in FIG. 4. The analog signal received from the optical sensor on signal line 700 is converted to a digital signal by analog-to-digital converter 702 in the processing channel 704. The digital signal is then received by the mixer circuit 706. The mixer circuit 706 also receives one or more demodulation operations 708. In general, the demodulation operation can be sin $$2\pi \frac{kt}{N} \text{ or } \cos 2\pi \frac{kt}{N},$$

where k is defined by 1≤k≤n/2, N represents the number of samples obtained by the optical sensor, and t=0, 1, . . . , N−1. The number of demodulation operations input into the mixer circuit 704 may be based on the number of light sources. In one embodiment, each harmonic of the signal received from the optical sensor has two orthogonal components. Thus, in some cases, the number of harmonics may depend upon the number of channels multiplexed and de-multiplexed. As one example, when the health monitoring system includes two light sources, the demodulation operations can be sin $2\pi/N$ or cos $2\pi/N$ for the first harmonic frequency. Two signals will be produced after both demodulation operations have been applied to the digital signal by mixer circuit 706. When the health monitoring system has four light sources, the demodulation operation can be sin $2\pi/N$ or cos $2\pi/N$ for the first harmonic frequency, and sin $4\pi/N$ or cos $4\pi/N$ for the second harmonic frequency. Four signals will be produced after the four demodulation operations have been applied to the digital signal by mixer circuit 706.

The signal output by the mixer circuit 706 is received by a low pass filter 710 and a decimation circuit 712. The low pass filter 710 and the decimation circuit 712 form a first decimation stage. Embodiments can include any number of decimation stages K. The number of decimation stages K can be based on the frequency of the sampling cycle of the optical sensor and the frequency of the physiological parameter. For example, in the embodiments shown in FIGS. 5 and 6, thirty samples are obtained by the optical sensor. When the frequency of the physiological parameter is approximately ten hertz and the frequency of the thirty sample cycle is 4096 hertz, six decimation stages are used with each stage reducing the frequency of the signal by two.

After the signal is processed by the low pass filter 714 and decimation circuit 716 in the last decimation stage K, each signal is received by a demultiplexer and multiplier circuit 718. The demultiplexer separates the signals by associated light source. Thus, the signal associated with the first light source is separated from the signals associated with the other light sources, and so on for each signal. The multiplier circuit then multiplies each signal by respective weights or values. As one example, the values can be stored in a matrix, and each signal is multiplied by the values in a respective row in the matrix.

The values in the matrix are a function of the dynamics and components of the health monitoring system. The operations of the components such as the optical sensor, the filters (e.g., high pass filters, low pass filters), the operational amplifiers, and the like, change over time due to temperature and other factors. The values in the matrix adjust the signals for these changes. One method for determining the values in the matrix is described in conjunction with FIG. 8.

The signals output on signal line 720 represent the signals received from the user's tissue, and these signals can be analyzed to determine or measure the physiological parameter. As one example, these signals can be analyzed to determine the heart rate of the user.

Figure 8:
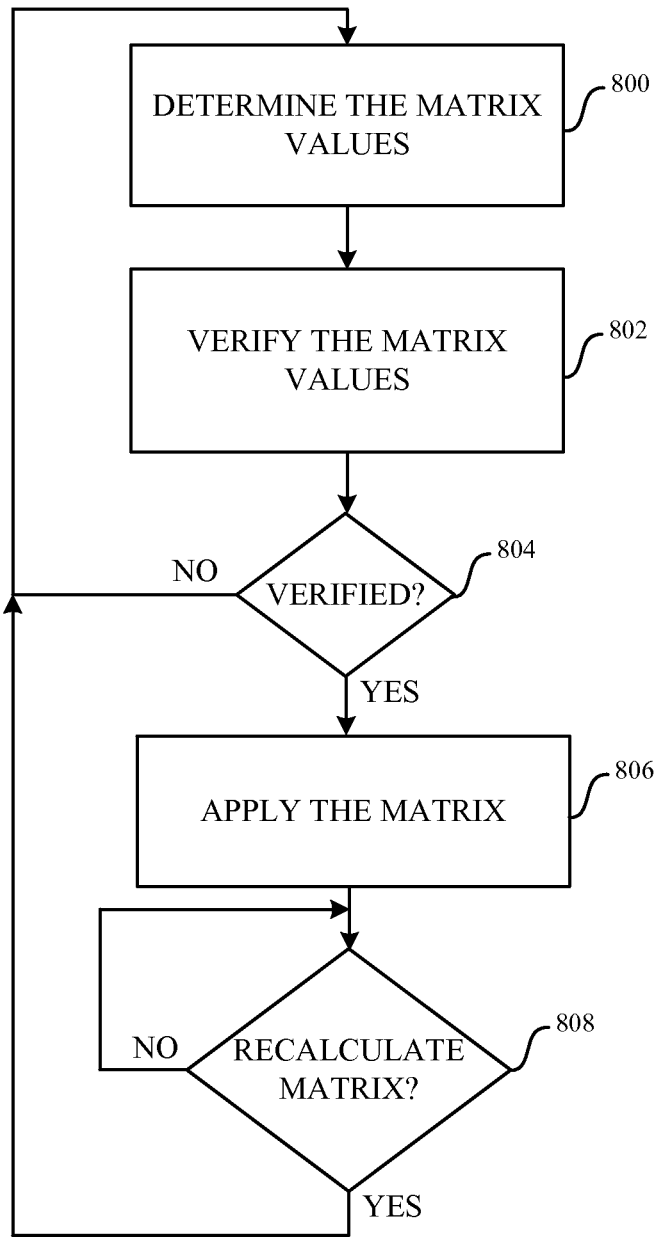
FIG. 8 is a flowchart of one example method of determining a matrix used in block 718 of FIG. 7.
Figure 9:
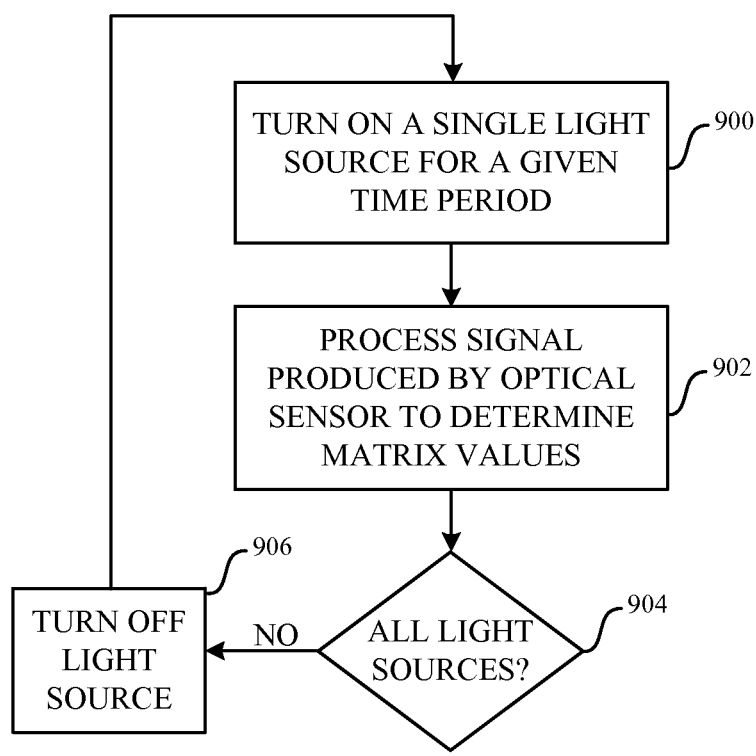
FIG. 9 is a flowchart of one example method of performing block 800 in FIG. 8.

FIG. 8 is a flowchart of one example method of determining the values in a matrix used in block 718 of FIG. 7. Initially, the values in the matrix are determined at block 800. FIG. 9 is a flowchart of one example method of performing block 800. In block 900, a single light source is turned on for a given period of time. The signal produced by the optical sensor is then processed to obtain some of the matrix values. For example, when the health monitoring system includes four light sources, s signal value or amplitude associated with each light source will be output by the decimation circuit 716. Thus, four signal values will be output by the decimation circuit 716 based on the single light source emitting light toward the user's skin. These four signal values are included in one row in the matrix.

Figure 10:
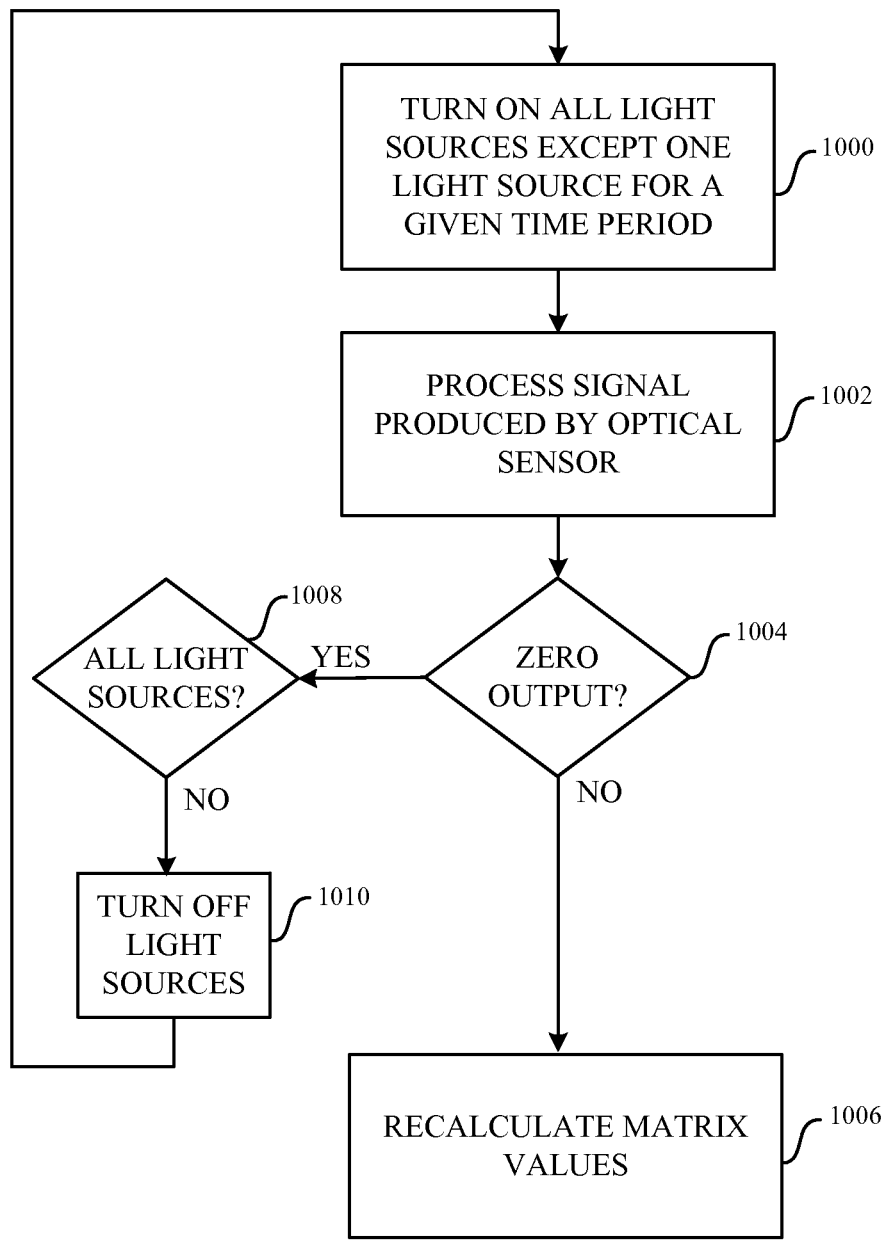
FIG. 10 is a flowchart of one example method of performing block 802 in FIG. 8.

Returning to FIG. 9, a determination is then made at block 904 as to whether or not all of the light sources have been individually turned on. If not, the process passes to block 906 where the light source that is currently turned on is turned off. The method then returns to block 900 where another single light source is turned on and the signal produced by the optical sensor processed to obtain matrix values for another row in the matrix. The method in FIG. 9 repeats until all of the light sources have been turned on and all of the values determined for the matrix. For four light sources, the values in the matrix are as follows:

Returning to FIG. 8, after the matrix values are determined at block 800 the matrix values can be verified at block 802. FIG. 10 is a flowchart of one example method of performing block 802. Initially, all of the light sources except one are turned on for a given period of time (block 1000). The signal produced by the optical sensor is then processed based on the data flow diagram shown in FIG. 7. As described earlier, the demultiplexer and multiplier circuit 718 outputs signals that are associated with each light source in the health monitoring system. The signal value associated with the light source that is turned off should have a value that is substantially zero, while the signal values associated with the light sources that are turned on should be greater than zero.

Returning to FIG. 10, a determination is made at block 1004 as to whether or not the signal value associated with the light source that is turned off equals zero. If not, the method passes to block 1006 where the matrix values in the matrix are recalculated. Thus, the method shown in FIG. 9 may be repeated and the method shown in FIG. 10 repeated until it is determined at block 1004 that the signal value associated with each light source equals zero when the respective light source is turned off and the other light sources are turned on.

If the signal value equals zero, the process continues at block 1008 where a determination is made as to whether or not all of the light sources have been turned off while the other light sources are turned on. If not, the method passes to block 1010 where the light sources that are currently turned on are turned off. The method then returns to block 1000 where all light sources except another single light source is turned on. The method in FIG. 10 repeats until all of the light sources have been turned off while the other light sources are turned on and the signal value output from the demultiplexer and multiplier circuit 718 associated with each light source equals zero when the respective light source is turned off and the other light sources are turned on.

Returning to FIG. 8, if the matrix values are not verified at block 804, the method returns to block 800 as described earlier. If the matrix values are verified at block 804, the process continues at block 806 where the matrix is applied in the demultiplexer and multiplier circuit 718 in FIG. 7. A determination may then be made at block 808 as to whether or not the matrix values are to be recalculated. As one example, the matrix values can be recalculated after a given period of time has passed. Additionally or alternatively, the matrix values may be recalculated each time a user activates the heath monitoring system. The process waits at block 808 if the matrix values are not recalculated. If the matrix values are to be recalculated, the method returns to block 800.

Various embodiments have been described in detail with particular reference to certain features thereof, but it will be understood that variations and modifications can be effected within the spirit and scope of the disclosure. For example, as described earlier, a health monitoring system can include a different number of light sources (e.g., two or six). Additionally or alternatively, a health monitoring system can be included in, or connected to a different type of electronic device.

Even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

What is claimed is:

1. A method for estimating physiological parameters when modulated light from a first light source and a second light source is emitted toward a body part of a user, the method comprising:
    determining a first multiplier value by:
        turning on the first light source;
        generating a first initial signal in response to capturing a first light sample corresponding to the first light source;
        demodulating the first initial signal to produce first initial demodulated signals;
        filtering and decimating the first initial demodulated signals; and
        determining the first multiplier value based on the filtered and decimated first initial demodulated signals;
    determining a second multiplier value by:
        turning on the second light source;
        generating a second initial signal in response to capturing a second light sample corresponding to the second light source;
        demodulating the second initial signal to produce second initial demodulated signals;
        filtering and decimating the second initial demodulated signals; and
        determining the second multiplier value based on the filtered and decimated second initial demodulated signals;
    capturing multiple light samples while the first light source and the second light source are turned on to emit modulated light toward the body part of the user and converting the multiple light samples into a captured signal;
    demodulating the captured signal to produce multiple demodulated signals;
    performing a first decimation stage by:
        low pass filtering each demodulated signal; and
        decimating each demodulated signal;
    performing a second decimation stage after the first decimation stage by:
        low pass filtering each demodulated signal; and
        decimating each demodulated signal;
    demultiplexing each demodulated signal after the second decimation stage to produce a first signal associated with the first light source and a second signal associated with the second light source;
    multiplying the first signal by the first multiplier value using a first multiplier circuit to obtain a first conditioned signal;
    multiplying the second signal by the second multiplier value using a second multiplier circuit to obtain a second conditioned signal; and
    analyzing the first conditioned signal and the second conditioned signal to estimate the physiological parameter of the user.

2. The method as in claim 1, wherein the capturing multiple light samples comprises capturing multiple light samples while:
    the first light source is turned on and the second light source is turned off;
    the second light source is turned on and the first light source is turned off; and
    the first light source and the second light source are turned off after being turned on.

3. The method as in claim 2, wherein the capturing multiple light samples further comprises capturing one or more light samples after the first light source is turned off and before the second light source is turned on.

4. The method as in claim 1, wherein the demodulating the captured signal to produce multiple demodulated signals comprises:
    applying a first demodulation operation of a sine function to the captured signal; and
    applying a second demodulation operation of a cosine function.

5. The method as in claim 2, wherein the multiple light samples comprise at least five light samples captured when the first light source is turned on and the second light source is turned off.

6. The method as in claim 1, wherein:
    when the first light source is turned on, the first light source emits infrared light; and when the second light source is turned on, the second light source emits visible light.

* * * * *